United States Patent [19]

Dwyer et al.

[11] Patent Number: 5,191,135
[45] Date of Patent: Mar. 2, 1993

[54] AROMATICS ALKYLATION PROCESS

[75] Inventors: Francis G. Dwyer, West Chester, Pa.; Quang N. Le, Cherry Hill, N.J.

[73] Assignee: Mobil Oil Corporation, Fairfax, Va.

[21] Appl. No.: 673,925

[22] Filed: Mar. 25, 1991

[51] Int. Cl.⁵ ............................................. C07C 2/66
[52] U.S. Cl. ................................. 585/455; 585/467
[58] Field of Search ............................ 585/467, 455

[56] References Cited

U.S. PATENT DOCUMENTS

| | | | |
|---|---|---|---|
| 4,211,665 | 7/1980 | Pellegrini, Jr. | 252/63 |
| 4,238,343 | 12/1980 | Pellegrini, Jr. | 585/24 |
| 4,301,316 | 11/1981 | Young | 585/455 |
| 4,421,941 | 12/1983 | Olson et al. | 585/467 |
| 4,570,027 | 2/1986 | Boucher et al. | 585/455 |
| 4,604,491 | 8/1986 | Dressler et al. | 585/26 |
| 4,714,794 | 12/1987 | Yoshida et al. | 585/26 |
| 4,774,379 | 9/1988 | Butler et al. | 585/467 |
| 4,783,566 | 11/1988 | Kocal et al. | 585/415 |
| 4,876,408 | 10/1989 | Ratcliffe et al. | 585/467 |
| 4,950,824 | 8/1990 | Shiroto et al. | 585/467 X |
| 4,962,256 | 10/1990 | Le et al. | 585/467 |
| 5,030,785 | 7/1991 | Huss et al. | 585/456 |

Primary Examiner—W. J. Shine
Assistant Examiner—Douglas J. McGinty
Attorney, Agent, or Firm—Alexander J. McKillop; Dennis P. Santini; Malcolm D. Keen

[57] ABSTRACT

Long chain alkyl substituted aromatic compounds, particularly alkylated naphthalenes, are produced by the alkylation of aromatics, e.g. naphthalene, with an olefin or other alkylating agent possessing at least 6 carbon atoms, usually 12 to 20 carbon atoms, in the presence of a zeolite alkylation catalyst, preferably a large pore size zeolite such as zeolite Y and in the presence of from about 0.5 to 3.0 weight percent water, preferably 1.0 to 3.0 weight percent. The use of the water co-feed increases the selectivity of the alkylation for the production of long chain mono-alkyl substituted naphthalenes in preference to more highly substituted products and also increases activity and catalyst stability.

24 Claims, No Drawings

AROMATICS ALKYLATION PROCESS

CROSS-REFERENCE TO RELATED APPLICATIONS

U.S. application Ser. No. 07/505,392, now U.S. Pat. No. 5,034,563 filed Apr. 6, 1990, relates to the production of alkylated naphthalenes with improved selectivity for the mono-alkylated product.

FIELD OF THE INVENTION

This invention relates to the production of alkylated aromatics, especially of alkylated naphthalenes and substituted naphthalenes.

BACKGROUND OF THE INVENTION

Alkylaromatic fluids have been proposed for use as certain types of functional fluids where good thermal and oxidative stability are required. For example, U.S. Pat. No. 4,714,794 (Yoshida) describes the monoalkylated naphthalenes as having excellent thermal and oxidative stability, low vapor pressure and flash point, good fluidity and high heat transfer capacity and other properties which render them suitable for use as thermal medium oils. The use of a mixture of monoalkylated and polyalkylated naphthalenes as a base for synthetic functional fluids is described in U.S. Pat. No. 4,604,491 (Dressler) and Pellegrini U.S. 4,211,665 and 4,238,343 describe the use of alkylaromatics as transformer oils.

The alkylated naphthalenes are usually produced by the alkylation of naphthalene or a substituted naphthalene in the presence of an acidic alkylation catalyst such as a Friedel-Krafts catalyst, for example, an acidic clay as described in Yoshida U.S. Pat. No. 4,714,794 or Dressler U.S. Pat. No. 4,604,491 or a Lewis acid such as aluminum trichloride as described in Pellegrini U.S. Pat. No. 4,211,665 and U.S. Pat. No. 4,238,343. The use of a catalyst described as a collapsed silica-alumina zeolite as the catalyst for the alkylation of aromatics such as naphthalene is disclosed in Boucher U.S. Pat. No. 4,570,027. The use of various zeolites including intermediate pore size zeolites such as ZSM-5 and large pore size zeolites such as zeolite L and ZSM-4 for the alkylation of various monocyclic aromatics such as benzene is disclosed in Young U.S. Pat. No. 4,301,316.

In the formulation of functional fluids based on the alkyl naphthalenes, it has been found that the preferred alkyl naphthalenes are the mono-substituted naphthalene since they provide the best combination of properties in the finished product: because the mono-alkylated naphthalenes posses fewer benzylic hydrogens than the corresponding di-substituted or polysubstituted versions, they have better oxidative stability and therefore form better functional fluids and additives. In addition, the mono-substituted naphthalenes have a kinematic viscosity in the desirable range of about 5–8 cSt (at 100° C.) when working with alkyl substituents of about 14 to 18 carbon atoms chain length. Although the mono-alkylated naphthalenes may be obtained in admixture with more highly alkylated naphthalenes using conventional Friedel-Krafts catalysts such as those mentioned above or by the use of zeolites such as USY, the selectivity to the desired mono-alkylated naphthalenes is not obtained.

Zeolite catalysts have been found to be effective for the production of mono-alkylated naphthalenes, as disclosed in U.S. Pat. No. 4,301,316 and, more recently, U.S. Pat. No. 4,962,256. Good selectivity for the preferred mono-substituted naphthalenes may be obtained by the incorporation of cations having a radius of at least 2.5 A in large pore size zeolites such as zeolite Y, as described in Ser. No. 07/505,392 now U.S. Pat. No. 5,034,563.

SUMMARY OF THE INVENTION

It has now been found that co-feeding of water during zeolite-catalyzed aromatic alkylation is very effective in controlling the product selectivity, i.e. the degree of alkyl substitution on the aromatic ring. When the alkylation reaction is carried out in the presence of zeolite catalysts as USY and MCM-22, the addition of water to the feed provides improved alkylation activity and selectivity for the production of the preferred mono-alkylated naphthalene synthetic lube base stocks and additives.

According to the present invention there is therefore provided a process for controlling the product selectivity of an aromatics alkylation process by co-feeding water during the reaction. The presence of water during the reaction not only alters the product selectivity toward mono-alkylated aromatic production but also enhances catalyst activity and stability by suppressing undesirable side reactions such as olefin oligomerization and coke formation. The option of water co-feeding to control product selectivity and viscosity provides greater process flexibility for the production of multiple-viscosity grade alkylaromatic lubes.

DETAILED DESCRIPTION

The starting materials for the production of the alkylaromatic products include various aromatic compounds such as the low and high molecular weight alkylbenzenes, including low molecular weight alkylbenzenes such as toluene and the isomeric xylenes and mixtures of such materials. Higher molecular weight alkylbenzenes typically with a molecular weight of from about 300 to 3,000, may be alkylated in this way as well as other aromatics including anthracene, phenanthrene and aromatics with other fused ring systems. The process is, however, of primary applicability with the production of alkylated naphthalenes since these products have been found to provide lubricant materials of very good stability which may be blended with other lubricant components such as the poly-alphaolefins. For convenience and brevity, the process is described below primarily with reference to the production of alkylated naphthalenes but it may also be used in a similar manner for the production of other alkylated aromatics.

The starting materials for the production of alkylated naphthalenes include naphthalene itself as well the substituted naphthalenes which may contain one or more short chain alkyl groups containing up to about eight carbon atoms, such as methyl, ethyl or propyl. Suitable alkyl-substituted naphthalenes include alpha-methylnaphthalene, dimethylnaphthalene and ethylnaphthalene. Naphthalene itself is preferred since the resulting mono-alkylated products have better thermal and oxidative stability than the more highly alkylated materials for the reasons set out above.

The alkylating agents which are used to alkylate the naphthalene include any aliphatic or aromatic organic compound having one or more available alkylating aliphatic groups capable of alkylating the naphthalene The alkylatable group itself should have at least about 6 carbon atoms, preferably at least about 8, and still more preferably at least about 12 carbon atoms. For the production of functional fluids and additives, the alkyl groups on the alkyl-naphthalene preferably have from about 12 to 30 usually 12 to 20, carbon atoms, with particular preference to about 14 to 18 carbon atoms. A preferred class of alkylating agents are the olefins with the requisite number of carbon atoms, for example, the hexenes, heptenes, octenes, nonenes, decenes, undecenes, dodecenes. Mixtures of the olefins, e.g. mixtures of $C_{12}$-$C_{20}$ or $C_{14}$-$C_{18}$ olefins, are useful. Branched alkylating agents, especially oligomerized olefins such as the trimers, tetramers, pentamers, etc., of light olefins such as ethylene, propylene, the butylenes, etc., are also useful. Other useful alkylating agents which may be used, although less easily, include alcohols (inclusive of monoalcohols, dialcohols, trialcohols, etc.) such as hexanols, heptanols, octanols, nonanols, decanols, undecanols and dodecanols; and alkyl halides such as hexyl chlorides, octyl chlorides, dodecyl chlorides; and higher homologs.

The alkylation reaction between the naphthalene and the alkylating agent is carried out in the presence of a zeolite catalyst which contains a cation of certain specified radius. The molecular size of the alkylation products will require a relatively large pore size in the zeolite in order for the products to leave the zeolite, indicating the need for a relatively large pore size in the zeolite, which will also tent to reduce diffusion limitations with the long chain alkylating agents. The large pore size zeolites are the most useful zeolite catalysts for this purpose although the less highly constrained intermediate pore size zeolites may also be used, as discussed below. The large pore size zeolites are zeolites such as faujasite, the synthetic faujasites (zeolites X and Y), zeolite L, ZSM-4, ZSM-18, ZSM-20, mordenite and offretite which are generally useful for this purpose are characterized by the presence of a 12-membered oxygen ring system in the molecular structure and by the existence of pores with a minimum dimension of at least 7.4 Å, as described by Frilette et. al., in *J. Catalysis* 67,218-222 (1981). See also Chen et. al., *Shape-selective Catalysis in Industrial Applications*, (Chemical industries; Vol. 36) Marcel Dekker Inc., New York 1989, ISBN 0-8247-7856-1 and Hoelderich et. al., *Agnew. Chem. Int. Ed. Engl.* 27 226-246 (1988), especially pp.226-229. The large pore size zeolites may also be characterized by a "Constraint Index" of not more than 2, in most cases not more than 1. Zeolite beta, a zeolite having a structure characterized by twelve-membered pore openings, is included in this class of zeolites although under certain circumstances it has a Constraint Index approaching the upper limit of 2 which is usually characteristic of this class of zeolites. The method for determining Constraint Index is described in U. S. Pat. No. 4,016,218, together with values for typical zeolites and of the significance of the Index in U.S. Pat. No.4,861,932, to which reference is made for a description of the test procedure and its interpretation.

Zeolites whose structure is that of a ten membered oxygen ring, generally regarded as the intermediate pore size zeolites may also be effective catalysts for this alkylation reaction if their structure is not too highly constrained. Thus, zeolites such as ZSM-12 (Constraint Index 2) may be effective catalysts for this reaction. The zeolite identified as MCM-22 is a particularly useful catalyst for this reaction because it gives a highly linear product with attachment to the alkyl chain at the 2-position. MCM-22 is described in U.S. Pat. No. 4,954,325, to which reference is made for a description of this zeolite. Thus, zeolites having a Constraint Index up to about 3 will generally be found to be useful catalysts, although the activity may be found to be dependent on the choice of alkylating agent, especially its chain length, a factor which imposes diffusion limitations upon the choice of zeolite.

The selectivity of the zeolite for the production of the preferred mono-alkylated alkylnaphthalene products is improved by the incorporation into the zeolite of cations of a certain minimum radius, at least 2.5 Å, as described in U.S. Ser. No. 07/505,392, to which reference is made for a description of the manner in which this improvement in selectivity can be made. The selected cations have a radius of least 2.5 Å, and preferably at least 3 0 Å. A number of cations conform to this requirement, including the hydrated cations of a number of metals, including monovalent, divalent and polyvalent, transitional and non-transitional metals. Even though the non-hydrated cations may not themselves conform to the ionic size requirement, the hydrated forms of the cations may do so. In particular, the relatively small radius cations of the alkali metals such as sodium and lithium (ionic radii of 0.95 and 0.60 Å, respectively) do not conform to the requirement, but the hydrated forms of these cations readily meet the requirement (radii of 3.58 and 3.82 Å). Cations of the required radius may also be provided by various organic species, especially the organic nitrogenous bases. A preferred class of cations of this type are the substituted ammonium cations, for example, alkylammonium cations, especially the short chain alkylammonium cations e.g. tetramethylammonium (TMA), tetraethylammonium (TEA) or tetrapropylammonium (TPA). The hydrated ammonium cation is also a suitable cationic form of the zeolite and is often preferred for zeolite Y or USY since these zeolites may be commercially available in the ammonium form as a precursor of the decationised or hydrogen form of the zeolite. The hydrated protonic form of the zeolite i.e. where the cation is the hydronium ion $H_3O$, is also effective as a catalyst.

The preferred zeolites for use in the present process are treated in this way to effect further improvements in the selectivity to the desired products.

A highly useful zeolite for the production of the mono-alkylated naphthalenes is zeolite Y in the ultrastable form, usually referred to as USY. When this material contains hydrated cations of the preferred minimum size, it catalyses the alkylation in good yields with excellent selectivity, as described in Ser. No. 07/505,392.

The zeolite may be composited with a matrix material or binder which is resistant to the temperatures and other conditions employed in the alkylation process. Such materials include active and inactive materials and synthetic or naturally occurring zeolites as well as inorganic materials such as clays, silica and/or metal oxides such as alumina, silica or silica-alumina. The latter may be either naturally occurring or in the form of gelatinous precipitates or gels including mixtures of silica and metal oxides. Use of an active material in conjunction with the zeolite may change the conversion and/or selectivity of the catalyst. Inactive materials suitably serve as diluents to control the amount of conversion so that alkylation products can be obtained economically and orderly without employing other means for controlling the rate of reaction. Binders which may be incorporated to improve the crush strength and other physically properties of the catalyst under commercial alkylation operating conditions include naturally occurring clays, e.g., bentonite and kaolin as well as the oxides referred to above.

The relative proportions of zeolite, present in finely divided crystalline form oxide matrix may vary widely, with the crystalline zeolite content ranging from about 1 to about 90 percent by weight and more usually, particularly when the composite is prepared in the form of beads, in the range of about 2 to about 80 weight percent of the composite.

The stability of the alkylation catalyst of the invention may be increased by steaming, as described in Ser. No. 07/505,932.

The alkylation is conducted such that the organic reactants, i.e., the alkylatable aromatic compound and the alkylating agent, are brought into contact with the zeolite catalyst in a suitable reaction zone such as, for example, in a batch type reactor or flow reactor containing a fixed bed of the catalyst composition, under effective alkylation conditions. Such conditions typically include a temperature of from 100° to 400° C., usually from 100° to 300° C., a pressure of from about 0.2 to 25, preferably 1 to 5, atmospheres, a feed weight hourly space velocity (WHSV) of from about 0.1 $hr^{-1}$ to about 10 $hr^{-1}$ aromatic compound to alkylating agent mole ratio of from about 0.1:1 to about 50:1, preferably from about 4:1 to about 1:4 e.g. from about 2:1 to about 1:2.

In a continuous, fixed bed type operation, the temperature will normally be in the range 200° to 600° F. (about 93° to 315° C.), preferably 300° to 400° F. (about 150° to about 205° C.), with pressures in the range of 50 to 1000 psig (about 450 to about 7,000 kPa abs). The WHSV is based upon the weight of the catalyst composition employed, i.e., the total weight of active catalyst (and binder if present) and is normally in the range of 0.1 to 5.0, preferably 0.5 to 5.0, with most cases in the range 0.25 to 1.50. Preferred reaction conditions include a temperature within the approximate range of from about 100° to about 350 C., a pressure of from about 1 to about 25 atmospheres, a WHSV of from about 0.5 $hr^1$ to about 5 $hr^{-1}$ and an alkylatable aromatic compound to alkylating agent mole ratio of from about 0.5:1 to about 5:1.

When using naphthalene as the aromatic compound, the pressure should preferably be maintained at a value of at least about 50 psig in order to prevent the naphthalene from subliming into the overhead of the alkylation reactor; the required pressure may be maintained by inert gas pressurization, preferably with nitrogen. The reactants can be in either the vapor phase or the liquid phase and can be neat, i.e., free from intentional admixture or dilution with other material, or they can be brought into contact with the zeolite catalyst composition with the aid of carrier gases or diluents such as, for example, hydrogen or nitrogen. The alkylation can be carried out as a batch-type reaction typically employing a closed, pressurized, stirred reactor with an inert gas blanketing system or in a semi-continuous or continuous operation utilizing a fixed or moving bed catalyst system.

The addition of water to the feed to the alkylation reaction suppresses the formation of poly-alkylated naphthalene product and shifts the product selectivity toward mono-alkylated naphthalene production. The mono-alkylated naphthalene selectivity typically increases from about 40 to 75% with 1 wt % water co-feed and the addition of additional water up to 2 wt % may be effective to increase the naphthalene conversion, typically from about 70 or 75 to about 90 or 95 weight percent. The water also suppresses olefin oligomerization reactions as evidenced by a significant reduction in the formation of the dimer, typically from about 10 to 6 weight, percent. The amount of water added to the feed is preferably at least about 0.1 weight percent in to produce a significant improvement and in most cases, at least 0.5 weight percent, based on the total hydrocarbon feed will be preferably employed, but will normally not exceed 5.0 weight percent of the feed, preferably not more than 3.0 weight percent of the feed, both for fixed bed, continuous and batch type operations. The amount of water is preferably from about 10 to 60 weight percent of the catalyst (including binder), and in most cases, from about 10 to about 40 weight percent of the catalyst, especially in batch type processes. The maximum amount of water should, however, be determined for each system since excessive amounts of water co-feed will cause a decrease in catalyst activity. With large excesses of water, the activity of the catalyst may be entirely suppressed. In most cases, the optimum amount of water should normally be in the range of about 1-3, preferably about 1-2 weight percent. Above these water levels, the excess water may block the zeolite acid sites either partly or completely, with a suppression of catalytic activity.

The products comprising alkylated aromatics are characterized by exceptional oxidative and thermal stability. They may be separated from the reaction mixture by stripping off unreacted alkylating agent and naphthalene compound in the conventional manner. It has also been found that the stability of the alkylated product may be improved by filtration over activated charcoal and by alkali treatment to remove impurities, especially acidic by-products formed by oxidation during the course of the reaction. The alkali treatment is preferably carried out by filtration over a solid alkali material, preferably calcium carbonate (lime). In a typical product work-up, it has been found, for example, that the RBOT (Rotating Bomb Oxidation Test) stability can be increased from a value of 184 minutes for an unstripped product ($C_{14}$-alkylnaphthalene) to 290 minutes if the unreacted materials are removed by stripping and to 350 minutes if the stripped product is filtered over lime ($CaCO_3$).

EXAMPLE 1

This example demonstrates the catalytic activity of a conventional, calcined USY zeolite for alkylating naphthalene with a long chain alpha olefin to produce alkylated naphthalene lube base stocks.

The catalyst used in this example was a USY catalyst containing about 40 weight percent USY component with an unit cell size of 24.55 Å. The catalyst was calcined at 1000 F for 24 hours prior to use. The alkylation experiment was carried out in an 1 liter autoclave using a $C_{14}$ olefin as the alkylating agent at a 2:1 molar ratio of $C_{14}=$:naphthalene, 5 weight percent catalyst at 400° F. for 6 hours under a nitrogen pressure of 1 atmosphere. After decanting and filtering the catalyst, the total liquid product was vacuum distilled at 600° F. to obtain 68 wt % lube base stock comprising of 31%, 23% and 5 weight percent mono-, di- and tri-alkylated naphthalene product, respectively. The lube also contains about 9 weight percent of C14 dimers due to olefin oligomerization reaction. This corresponds to the conversion of 79 weight percent naphthalene and 65 weight percent alpha C14 olefin. Table 1 shows the product properties of this alkylated naphthalene lube base stock.

TABLE 1

| Product Yield, wt % | |
|---|---|
| Mono-alkylated | 31 |
| Di-Alkylated | 23 |
| Tri-Alkylated | 5 |
| C14 Dimer | 9 |
| Lube Properties | |
| Pour Point, °F. | −50 |
| KV @ 40° C., cSt | 35.54 |
| KV @ 100° C., cSt | 5.68 |
| Viscosity Index | 97 |

This alkylated naphthalene synthetic lube base stock has excellent low-temperature characteristic as indicated by a very low pour point product (−50° F.).

EXAMPLE 2

In this example, the alkylation reactions were carried out under identical process conditions as in Example 1 except that water in the range of 1–4 weight percent based on the feed was added to the reactant mixture prior to the alkylation. Table 2 shows the affect of water addition on the performance of the USY catalyst.

TABLE 2

| Example No | 1 | 2A | 2B | 2C |
|---|---|---|---|---|
| H2O, wt % on feed | 0 | 1.0 | 2.0 | 4.0 |
| Conversion, wt % | | | | |
| Naphthalene | 79 | 96 | 96 | 0 |
| Alpha C14 Olefin | 65 | 59 | 62 | 0 |
| Product Distribution, wt % | | | | |
| Mono-Alkylated | 46 | 75 | 77 | 0 |
| Di-Alkylated | 34 | 19 | 16 | 0 |
| Tri-Alkylated | 7 | — | — | 0 |
| C14 Dimer | 13 | 6 | 7 | 0 |
| Total Alkylated Lube, wt % | 59 | 64 | 64 | 0 |

The results indicate that the addition of water suppresses the formation of poly-alkylated naphthalene product and shifts the product selectivity toward mono-alkylated naphthalene production. The mono-alkylated naphthalene selectivity increases from 46 to 75% with 1 weight percent water co-feeding. Furthermore, the addition of additional water up to 2 weight percent increases the naphthalene conversion from 79 to 96 weight percent and suppresses the olefin oligomerization reaction as evidenced by a significant reduction of dimer formation (from 13 to 6–7 weight percent). For this particular USY catalyst the optimum water concentration is in the range of 1–2 weight percent. Above this water level, the excess water may completely block the zeolite acid sites and consequently totally suppresses catalyst alkylation activity as seen in Example 2C.

EXAMPLE 3

This example illustrates the effectiveness of water addition on the naphthalene alkylation performance of MCM-22 zeolite catalyst. The autoclave experiment was carried out in a similar as in Example 1. The process conditions and the alkylation performance of MCM-22 with and without water co-feeding as shown in Table 2/

TABLE 3

| Example No. | 3A | 3B | 3C |
|---|---|---|---|
| Water, wt % on feed | 0 | 1.5 | 3.0 |
| Temp, °F. | 350 | 300 | 300 |
| MCM-22, wt % | 0.5 | 1.8 | 1.8 |

TABLE 3-continued

| Example No. | 3A | 3B | 3C |
|---|---|---|---|
| Conversion, wt % | | | |
| Naphthalene | 75 | 79 | 4 |
| Alpha C14 Olefin | 46 | 45 | 7 |
| Product Dist., wt % | | | |
| Mono-Alkylated | 76 | 87 | 100 |
| Di-Alkylated | 17 | 8 | — |
| Tri-Alkylated | 3 | — | — |
| C14 Dimer | 4 | 5 | — |

The results indicate MCM-22 has very high naphthalene alkylation activity and very good product selectivity toward mono-alkylated naphthalene products (Example 3A). The presence of 1.5 weight percent water enhances further catalyst mono-alkylated naphthalene products (Example 3A). The presence of 1.5 weight percent water enhances further catalyst mono-alkylated selectivity from 76 to 87% (Example 3B). Similar to USY zeolite shown in Example 2, the excess water co-feeding (3 weight percent completely deactivates the catalyst activity as shown by Example 3C.

We claim:

1. A process for preparing long chain alkyl-substituted naphthalenes with improved selectivity for the mono-alkylated product, which comprises reacting a naphthalene or alkyl naphthalene compound with an alkylating agent possessing an alkylating aliphatic group having at least sic carbon atoms under alkylation reaction conditions in the presence of water and a alkylation catalyst consisting essentially of a porous crystalline zeolite, to form a long chain alkylated naphthalene compound possessing at least one alkyl group derived from the alkylating agent, the selectivity for the mono-alkylated product being greater than in the absence of the added water.

2. A process according to claim 1 in which the zeolite is a large pore size zeolite having pores with a minimum dimension of at least 7.4 Å.

3. A process according to claim 1 in which the zeolite has a Constraint Index of not more than 2.

4. A process according to claim 1 in which the zeolite comprises zeolite X or zeolite Y and a binder.

5. A process according to claim 4 in which the zeolite comprises zeolite USY and a binder.

6. A process according to claim 1 in which the zeolite comprises zeolite MCM-22 and a binder.

7. A process according to claim 1 in which the alkylation is carried out in the presence of from 0.5 to 3.0 weight percent water, based on the total hydrocarbon feed.

8. A process according to claim 7 in which the alkylation is carried out in the presence of from 1.0 to 3.0 weight percent water, based on the total hydrocarbon feed.

9. A process according to claim 8 in which the alkylation is carried out in the presence of from 10 to 60 weight percent water, based on the weight of the catalyst.

10. A process according to claim 1 in which the alkylating aliphatic group contains at least about 8 carbon atoms.

11. A process according to claim 10 in which the alkylating aliphatic group contains at least about 12 carbon atoms.

12. A process according to claim 11 in which the alkylating aliphatic group contains from 14 to 18 carbon atoms.

13. A process according to claim 1 in which the alkylating agent comprises an olefin.

14. A process according to claim 1 in which the alkylation reaction conditions includes a temperature of from about 100° C. to about 400° C., a pressure of from about 0.2 to about 25 atmospheres, an WHSV of from about 0.1 to 10 and an alkylatable aromatic compound to alkylating agent mole ratio of from about 0.1:1 to 50:1.

15. A process according to claim 14 in which the alkylation reaction conditions includes a temperature of from about 100° C. to 300° C., a pressure of from about 1 to 5 atmospheres, a WHSV of from about 0.5 to about 5 and an alkylatable aromatic compound to alkylating agent mole ratio of from about 0.5:1 to 5:1.

16. A process according to claim 1 in which the zeolite alkylation catalyst comprises a porous crystalline zeolite containing cations having a radius of at least 2.50 Å.

17. A process according to claim 16 in which the cations have a radius of at least 3.0 Å.

18. A process for preparing long chain alkyl substituted naphthalenes with improved selectivity for the mono-alkylated product which comprises reacting naphthalene with a olefin containing from about 12 to about 20 carbon toms as an alkylating agent under alkylation reaction conditions in the presence of from 1.0 to 3.0 weight percent water, based on the amount of the naphthalene and the alkylating agent and in the presence of an alkylation catalyst consisting essentially of (i) a porous crystalline zeolite having a minimum pore dimension of at least 7.4 Å and the crystal structure of zeolite Y and (ii) a binder material, to form an alkylated naphthalene possessing at least one alkyl group derived from the alkylating agent the selectivity for the mono-alkylated product being greater than in the absence of the added water.

19. A process according to claim 1 in which the aromatic compound comprises naphthalene.

20. A process for preparing long chain alkyl substituted naphthalenes with improved selectivity for the mono-alkylated product which comprises reacting naphthalene with a olefin containing at least 8 carbon toms as an alkylating agent under alkylation reaction conditions and in the presence of from 1.0 to 3.0 weight percent water, based on the amount of the naphthalene and the alkylating agent, and an alkylation catalyst consisting essentially of a porous crystalline zeolite and a binder material, to form an alkylated naphthalene possessing at least one alkyl group derived from the alkylating agent, the selectivity for the mono-alkylated product being greater than in the absence of the added water.

21. A process according to claim 20 in which the alkylation is carried out in the presence of from 10 to 60 weight percent water, based on the weight of the catalyst.

22. A process according to claim 20 in which the zeolite is a large pore size zeolite having a minimum pore dimension of at least 7.4 Å.

23. A process according to claim 20 in which the zeolite is zeolite MCM-22.

24. A process according to claim 24 in which the alkylation reaction conditions include a temperature of from about 100° C. to about 400° C., a pressure of from about 0.2 to about 25 atmospheres, and from 10 to 60 weight percent water, based on the weight of the catalyst.

* * * * *

UNITED STATES PATENT AND TRADEMARK OFFICE
CERTIFICATE OF CORRECTION

PATENT NO. : 5,191,135

DATED :  March 2, 1993

INVENTOR(S) : F.G. Dwyer et al.

It is certified that error appears in the above-identified patent and that said Letters Patent is hereby corrected as shown below:

Col. 8, claim 1, line 30    "sic" should be --six--

Col. 8, claim 1, line 31    "a" should be --an--

Col. 9, claim 18, line 29    "toms" should be --atoms--

Col. 10, claim 24, line 30    "24" should be --18--

Signed and Sealed this

Eleventh Day of January, 1994

Attest:

BRUCE LEHMAN

Attesting Officer     Commissioner of Patents and Trademarks